US011076905B2

(12) United States Patent
Fischer et al.

(10) Patent No.: US 11,076,905 B2
(45) Date of Patent: Aug. 3, 2021

(54) CRYOPROBE AND METHOD OF MANUFACTURING THE SAME

(71) Applicant: Erbe Elektromedizin GmbH, Tübingen (DE)

(72) Inventors: Klaus Fischer, Nagold (DE); Jörg Kronenthaler, Hirrlingen (DE); Achim Brodbeck, Metzingen (DE); Marcus Adler, Tübingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 549 days.

(21) Appl. No.: 15/816,720

(22) Filed: Nov. 17, 2017

(65) Prior Publication Data

US 2018/0140342 A1    May 24, 2018

(30) Foreign Application Priority Data

Nov. 18, 2016  (EP) .................................. 16199575

(51) Int. Cl.
*A61B 18/02* (2006.01)
*A61B 17/00* (2006.01)
*A61B 18/00* (2006.01)

(52) U.S. Cl.
CPC .... *A61B 18/02* (2013.01); *A61B 2017/00526* (2013.01); *A61B 2018/00166* (2013.01);
(Continued)

(58) Field of Classification Search
CPC ............ A61B 18/02; A61B 2018/0231; A61B 2018/0212
See application file for complete search history.

(56) References Cited

U.S. PATENT DOCUMENTS 5,573,532 A  *  11/1996  Chang .................... A61B 18/02
                                                              228/221
5,857,997 A  *   1/1999  Cimino ................ A61B 5/0422
                                                              604/95.01
(Continued)

FOREIGN PATENT DOCUMENTS

CN     102548607 A    7/2012
DE    102008026635 A1  1/2009
(Continued)

OTHER PUBLICATIONS

European Communication pursuant to Article 94(3) EPC dated Oct. 23, 2019, in corresponding European Application No. 16199575.8, with machine English translation (9 pages).
(Continued)

*Primary Examiner* — Michael F Peffley
*Assistant Examiner* — Bo Ouyang
(74) *Attorney, Agent, or Firm* — Fitch, Even, Tabin & Flannery LLP

(57) ABSTRACT

The inventive method of manufacturing a cryoprobe uses an assembly pin (25) for receiving a sleeve (20) that is to form a part of the head (13) of the cryoprobe and comprises three abutment surfaces (27, 29, 30) that are axially offset relative to each other, said abutment surfaces ensuring, following the attachment of the sleeve (20) and the nozzle (24) to the tube end (19), the correct axial positioning of the nozzle (24) and the sleeve (20), in particular, relative to the distal end surface (18) of the tube end (19). Consequently, the position of the nozzle (24) in the expansion chamber (23) that formed after the sleeve (20) was closed and thus the function of the cryoprobe are ensured.

8 Claims, 3 Drawing Sheets

(52) U.S. Cl.
CPC ............... *A61B 2018/0212* (2013.01); *A61B 2018/0262* (2013.01); *A61B 2018/0268* (2013.01)

(56) References Cited

U.S. PATENT DOCUMENTS

| | | | |
|---|---|---|---|
| 6,241,722 B1 | 6/2001 | Dobak et al. | |
| 7,220,257 B1* | 5/2007 | Lafontaine | A61B 18/02 606/21 |
| 9,402,676 B2 | 8/2016 | Babkin et al. | |
| 2009/0287202 A1* | 11/2009 | Ingle | A61B 18/02 606/21 |
| 2010/0198202 A1 | 8/2010 | Fischer et al. | |
| 2012/0071868 A1 | 3/2012 | Fischer et al. | |
| 2012/0245584 A1* | 9/2012 | Kegreiss | A61B 18/12 606/41 |
| 2012/0253336 A1 | 10/2012 | Littrup et al. | |
| 2014/0378970 A1 | 12/2014 | Thompson | |

FOREIGN PATENT DOCUMENTS

| | | |
|---|---|---|
| DE | 102009018291 A1 | 10/2010 |
| JP | 2011-520513 A | 7/2011 |
| JP | 2013-505749 A | 2/2013 |
| JP | 2013-539387 A | 10/2013 |

OTHER PUBLICATIONS

Search Report in corresponding European Application No. 16199575.8, dated May 23, 2017, 9 pages.

Chinese First Office Action and Search Report dated Apr. 20, 2020, in corresponding Chinese Application No. 201711146249.3, with English translation (22 pages).

Japanese Office Action dated May 11, 2021, in corresponding Japanese Application No. 2017-218935, with machine English translation (7 pages).

* cited by examiner

CRYOPROBE AND METHOD OF MANUFACTURING THE SAME

RELATED APPLICATION(S)

This application claims the benefit of European Patent Application No. EP 16199575.8 filed Nov. 18, 2016, the contents of which are incorporated herein by reference as if fully rewritten herein.

TECHNICAL FIELD

The invention relates to a method of manufacturing a cryoprobe, as well as to a cryoprobe.

BACKGROUND

In medicine cryoprobes are disposed for acting by means of cold on biological tissue. Such a cryoprobe can be inferred from publication DE 10 2009 018 291 A1. This cryoprobe comprises a flexible tube having, on its distal end, a metal head that is specially configured for the respectively specific application, which head can be internally cooled via a coolant. In doing so, it can be achieved that biological tissue will freeze to the head and be separated and removed from the surrounding tissue for the purpose of a biopsy, for example.

The connection between the distally provided head and the flexible tube must be fluid-tight and exhibit tensile strength. In addition, frequently cryoprobes with an extremely small diameter are desired in order to be able to also advance the probe in a patient's tight lumens and vessels.

Furthermore, it is frequently desirable on the part of the manufacturer to provide cryoprobes in sterile form, so that the cryoprobe can be used on the patient without additional sterilization treatment. The aim is to cost-effectively provide such instruments as disposable products.

SUMMARY

Considering this, the object of the invention is to state a method of providing cryoprobes, said method allowing the simple manufacture of same with process reliability. Furthermore, it is the object of the invention to provide a cryoprobe that can be produced with the method according to the invention and satisfies at least a few of the otherwise aforementioned requirements.

According to the invention, the method provides that the manufacture of a cryoprobe is based on a tube device having at least two channels, wherein a nozzle in the form of a separate, preferably pre-manufactured component, is inserted in one of the channels and the tube end is provided with a sleeve on the outside in such a manner that the sleeve accommodates the tube end and projects distally beyond the tube end, in particular beyond its face-side, preferably flat, end face. Thereafter, the sleeve is deformed inward during a forming process in such a manner that it is fixed on the tube end by means of a compression connection. Alternatively, the sleeve may have—even before assembly—an inside diameter that is smaller than the outside diameter of the tube end that is then axially pressed into this sleeve. In both cases the sleeve has an inside diameter—at the latest in completely assembled state—that is smaller than the outside diameter of the tube device. Consequently, a press fit of the sleeve on the tube end is ensured.

In principle, the sleeve may be closed, or be subsequently closed, on its distal end. This may be accomplished with an end cap that is connected to the sleeve in a sealing manner for the distal closure of the sleeve by means of an annular sealing connection, e.g., a weld seam. Preferably, the weld seam is provided after the sleeve has been applied to the tube end. Alternatively, the end may also be connected to the sleeve before applying the sleeve according to one of the aforementioned methods, for example by means of an annular weld seam. It is also possible to configure the sleeve and the end cap in one piece, i.e., without seams and in one piece, and of the same material.

As an alternative to the metal crimping sleeve, it is also possible to use a probe tip of a thermally conductive plastic material and a plastic coating. Leak-tightness and compressive strength are then achieved, for example, by ultrasonic welding.

The manufacture of the cryoprobe by means of said method is preferred with a sleeve that is open on both sides. Then the sleeve can be received by an assembly pin that has an abutment surface for the sleeve where the sleeve comes into firm face-side abutment and is disposed for axially positioning the sleeve on the tube end during assembly. The assembly pin may have a projection within this annular abutment surface, said projection being disposed for the face-side abutment of the tube end, so that the desired distance of the end surface of the sleeve from the face surface of the tube end is ensured. In this manner, it can be ensured during a simple joining process that the sleeve will exhibit a desired overlap relative to the tube end.

Also, during this process step, the insertion of the nozzle into the tube end may take place with the aid of the assembly pin. A nozzle that has been accepted by the pin or has been previously placed with one end in the tube end can be inserted, during the joining process of the sleeve and the tube by a nozzle abutment surface of the assembly pin, into the tube end, so that the nozzle projects over the tube end in an axially precise manner by a desired measure, i.e., in particular, a precise axial overlap over the end face of the tube end. Due to this joining process by means of the assembly pin that has three separate abutment surfaces (for the sleeve, the tube end and the nozzle) it is achieved that the sleeve, the nozzle, as well as the face surface of the tube end are positioned precisely in the desired dimensional relationship with respect to each other. Consequently, after closing the sleeve by means of the cap, flow conditions defined by the cap are generated in the thusly provided expansion chamber, so that it is possible—in a simple manner—to ensure the correct thermal function of the cryoprobe. In particular, it can be ensured that the cryoprobe cools uniformly or with a desired cold distribution and thus produces the desired surgical effect during subsequent use.

If desired, the cryoprobe that is to be manufactured in this manner may be be produced with the use of adhesives. The seal between the expansion chamber and the tube is accomplished by the plastic material of the tube itself—to the extent that it as such acts as a seal. The seal between the cap and sleeve is accomplished by the weld seam, for example. The seal between the nozzle and the inside wall of the channel of the tube is provided by the tube material itself, said material also acting as a seal to this extent.

If desired, the manufacturing method can be used without liquid sealing and adhesive materials during production and is suitable for use in clean rooms. This facilitates the manufacture as a sterile product and reduces expenses therefor.

The tube device of the cryoprobe may be configured as a single tube having two or more channels. However, it is also possible to provide two or more tubes that are connected to each other. To accomplish this, for example, they are held on the tube end in a plastic body that is disposed to accommodate the sleeve. The remaining embodiment types explained hereinabove or hereinafter are provided in such a tube device as are in a one-piece tube having two or more channels.

The nozzle is a separate component and can be provided, especially on its otherwise cylindrical circumferential outside surface, with an anchoring structure for engagement in the tube end. For example, the anchoring structure may be provided in locally or peripherally extending, for example annular, ribs that, for example, have a triangular cross-section. The anchoring structure may also consist of micro-recesses or elevations, i.e., a rough region or knurling that is provided on the entire circumferential outside surface or in zones thereof.

In particular in the region in which the sleeve has been deformed inward, i.e., in the forming zone in which it exerts a radially inward-directed force, it may be provided with a support structure. This support structure may be formed by the nozzle itself. As a result of this, the nozzle is held firmly in the channel and, if present, by its anchoring structure. Due to the radially inward-directed deformation of the sleeve, a) the sleeves becomes axially non-slidable on the tube with the later applied end cap and b) the nozzle is secured axially non-slidably in the channel of the tube.

Furthermore, support structures may be arranged in the free channels, i.e., the channels that do not accommodate the nozzle. Suitable support structures are, for example, metal pipe sections, wire structures, e.g., in the vein of a helical spring, or also a plastic lining of the channel in question with a plastic material exhibiting a stiffness that is greater than the stiffness of the remaining tube material. In particular in the case of the stiff plastic lining, the support structure may extend along the entire length of the tube. Such a single-channel or multi-channel tube may be provided, for example, as a co-extrudate.

The radially inward-directed deformation of the sleeve may be accomplished by forming tools comprising to two or more clamping jaws arranged around the circumference of the sleeve, said clamping jaws deforming the sleeve during a compression process in such a manner that the inside diameter of said sleeve decreases and the tube end is clamped in place. The deforming may also be accomplished by rolling, e.g., by means of one or more rolls circulating along the circumference of the sleeve. Alternatively, the deformation may be done in a contactless manner by means of electromagnetic forming. To do so, the sleeve may be placed in a magnetic coil to which a current pulse is applied that induces vortical currents in the sleeve. The vortical current alternately interacts with the spool current due to Lorentz force and deforms the sleeve radially inward at least in an annular zone.

Alternatively, the sleeve may be fabricated of a shape memory material, in particular a shape memory metal, e.g., a nickel titanium alloy (nitinol). Then, for example, the sleeve is provided in a cold-widened condition having an inside diameter that is greater than the outside diameter of the tube, wherein said sleeve—when heated—again returns to its original shape in which the inside diameter is smaller than the outside diameter of the tube.

BRIEF DESCRIPTION OF THE DRAWINGS

Additional details of advantageous embodiments are the subject matter of the claims or the description of the drawings. They show in FIG. 1 a schematic diagram of the cryoprobe according to the invention;

FIGS. 7 and 8a perspective illustration of various embodiments of the tube devices for providing the cryoprobe;

DETAILED DESCRIPTION

Figure 1:
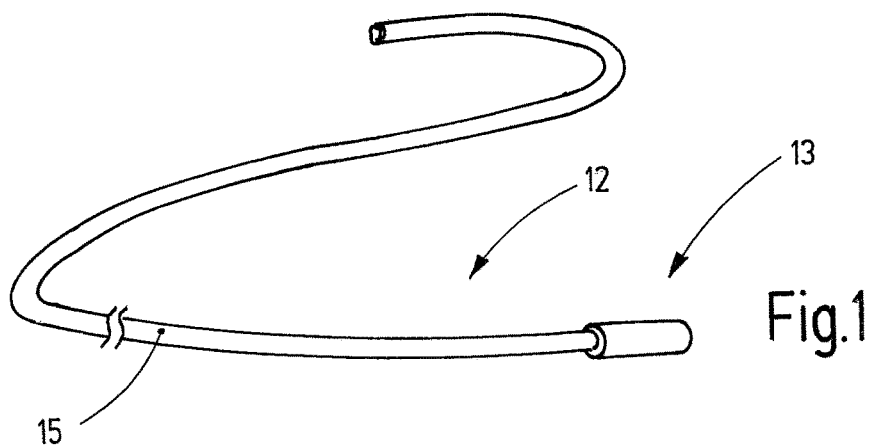

FIG. 1 shows a cryoprobe 12 that can be used, for example, for the cryogenic treatment of biological tissue. For example, the cryoprobe 12 can be used in a bronchoscope for the removal of a tissue sample. To do so, the cryoprobe 12 is inserted, for example, by means of a flexible bronchoscope into the lung, for example up to the pleura, where the head 13 is then brought into contact with biological tissue. With the use of an expanding or evaporating, i.e., gaseous or liquid cryofluid such as, e.g., $N_2$ or $CO_2$, at least one section of the head 13 is cooled to such an extent that biological tissue in contact therewith freezes and, if the removal of tissue is desired, adheres to the head 13 and can be removed, together with the head, from the pleura.

Figure 2:
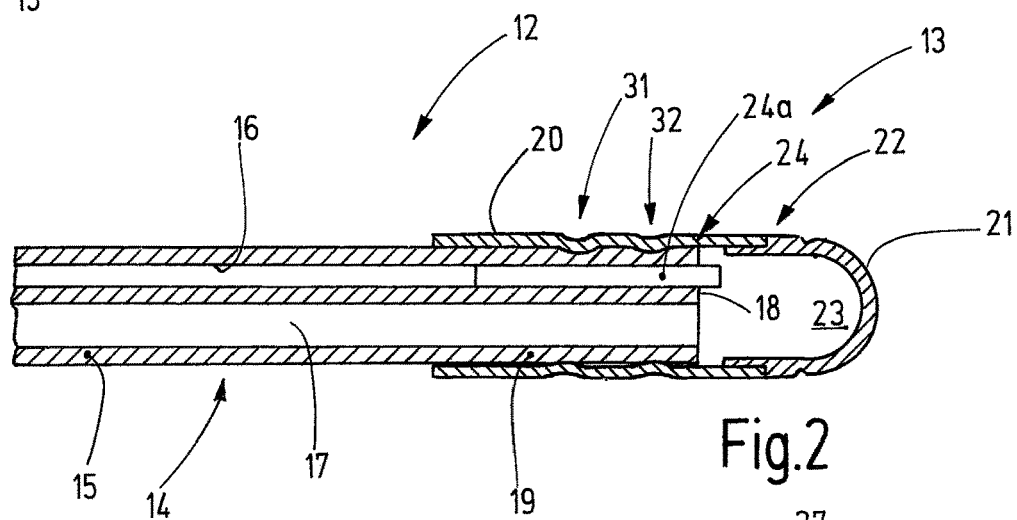
FIG. 2 a longitudinal illustration of a section of the cryoprobe according to FIG. 1.

FIG. 2 shows an exemplary design of the cryoprobe 12. The cryoprobe 12 comprises a tube device 14 that, in the present exemplary embodiment, is formed by a flexible plastic tube 15 that has a first channel 16, as well as a second channel 17. The two channels 16, 17 may have different diameters. Preferably, the cross-section of the second channel 17 is 1.1 to 2.5 times greater than the cross-section of the first channel 16. Both channels 16, 17 preferably extend parallel to each other and at a distance next to each other through the entire length of the plastic tube 15 and both terminate at the distal, preferably flat, face surface 18 of said tube.

The plastic tube 15 has a tube end 19 that bears the head 13 of the cryoprobe 12. The head 13 comprises a sleeve 20 that is held on the tube end 19 and extends beyond the face surface 18. The sleeve 20 bears an end cap 21 that is connected to the sleeve in a fluid-tight manner. To accomplish this, the end cap 21 preferably is welded, on the distal end of the sleeve 20, to said sleeve, for example by means of an annular laser weld seam or another weld seam. Thus, the end cap 21 distally delimits an expansion chamber 23 for the cryofluid that is supplied via the first channel 16 and injected via the nozzle 24 into the expansion chamber 23. The nozzle is a component that may consist of metal, ceramic or also of a plastic material, in which case the plastic material preferably is a plastic material that is different from the material of the plastic tube.

The nozzle shaft 24a of the nozzle 24 is held, e.g., clamped, to the end section of the first channel 16 adjoining the distal face surface 18. On the end side, the nozzle 24 may end with the distal face surface 18 or, as is preferred and shown by FIG. 2, project slightly from the channel 16 into the expansion chamber 23. In doing so, the axial position of the nozzle affects the flow conditions in the expansion chamber 23 and is thus essential for the correct function.

Preferably, the nozzle 24 has an essentially round nozzle orifice that is centrally arranged in the nozzle 24 and thus centrally relative to the channel in which the nozzle is held. This simplifies the manufacture because an alignment of the nozzle is not necessary prior to its insertion in the channel 16. However, an asymmetrical arrangement is also possible, this potentially benefiting the cooling distribution.

Figure 3:
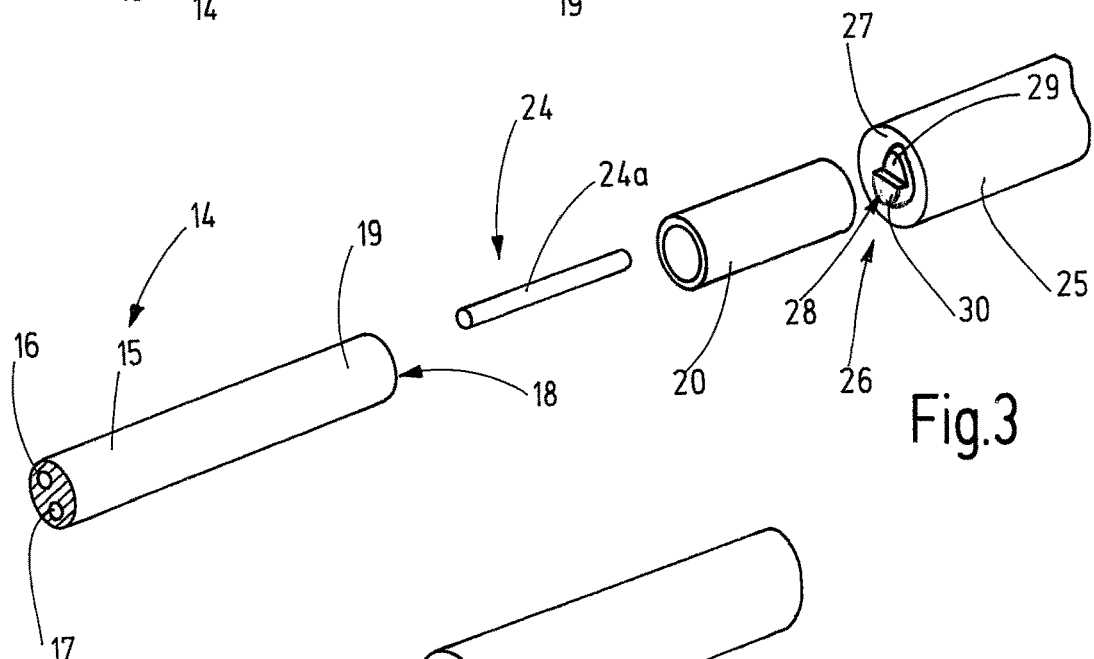
FIG. 3 an exploded view of a process step of the manufacturing process for providing the cryoprobe according to FIGS. 1 and 2, with the use of an assembly pin.

The manufacture of the cryoprobe 12 described so far is shown, at least in part, by FIG. 3. To do so, the plastic tube 15 is first provided with the nozzle 24 that is inserted into the channel 16 at least far enough so as to at least temporarily hold said nozzle in said tube. Furthermore, the sleeve 20 is set on an assembly pin 25 that comprises a sleeve receptacle 26 for this purpose. The latter comprises an annular, preferably flat, compression surface 27 that extends around a projection 28. For example, this projection 28 has a cylindrical circumferential surface having an outside diameter corresponding to the inside diameter of the sleeve 20, so that the sleeve 20 may be plugged onto the projection 28 to be then held on said projection. Together, the projection and the compression surface 27 form a seat for the sleeve 20.

The projection 28 is preferably provided with an offset on its face side. Said projection comprises a first abutment surface 29 for the nozzle 24 and a second abutment surface 30 that is to come into contact with the distal face surface 18 of the plastic tube 15 in the region of the second channel 17.

Figure 5:
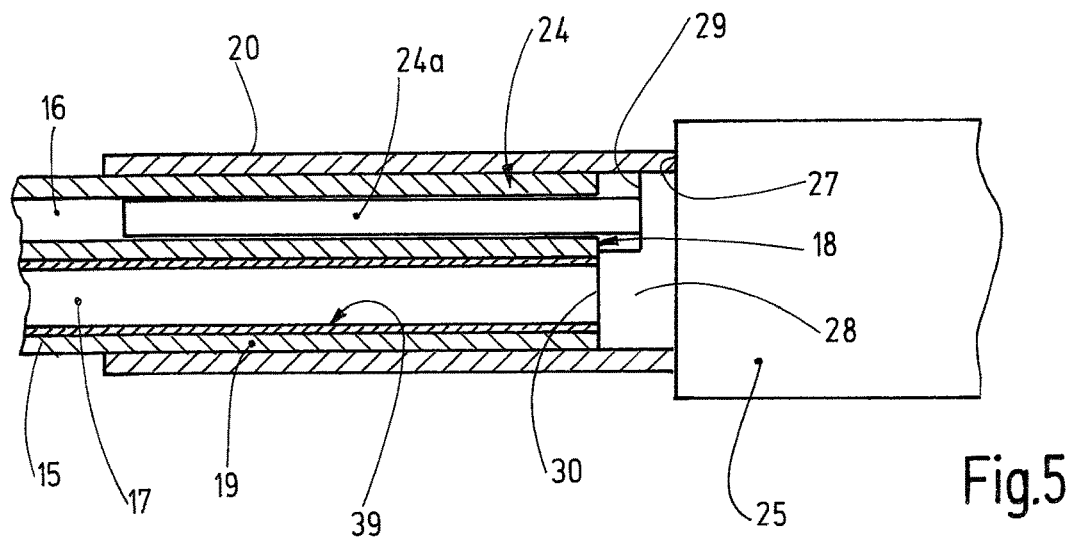
FIG. 5 the cryoprobe according to FIG. 2 during the manufacture with an assembly pin according to FIG. 3 and a tube with inherent internal support.

The attachment of the sleeve 20 and the nozzle 24 to the tube end 19 of the plastic tube 15 can be inferred from FIG. 5. The plastic tube 15 into which the nozzle shaft 24a of the nozzle 24 is partially inserted and the assembly pin 25 that is provided with the sleeve 20 are axially moved toward each other in such a manner that, first, the tube end 19 moves into the sleeve 20 and the first abutment surface 29 comes into contact with the end surface of the nozzle 24. Then the axial movement is continued until the second abutment surface 30 of the projection 28 comes into contact with the distal face surface 18 of the plastic tube 15. In this state, the sleeve 20 and the nozzle 24 display well-defined axial positions relative to the distal face surface 18, thereby providing an essential basis for the later correct function of the cryoprobe 12.

The joining process described so far can be employed in a first embodiment wherein the sleeve 20 has a smaller diameter than the outside diameter of the plastic tube 15, as well as in a second embodiment, wherein the inside diameter of the sleeve 20 is at least as great as the outside diameter of the plastic tube 15.

Referring to the first-mentioned embodiment, the sleeve 20 may have, on its proximal end, a not specifically illustrated insertion chamfer. Alternatively or additionally, the distal face surface 18 of the plastic tube 15 may transition—on its radially outer edge—into a conical surface that forms a tube-side insertion chamfer. As a result of this, it is possible to secure the sleeve 20 by press-fitting it on the tube end 19 and by press-fitting the nozzle 24 in the tube end 19. Referring to the second, already aforementioned, embodiment, the sleeve 20 is deformed radially inward—at least in parts—following its application to the tube end 19 and thus constricted. FIG. 2 shows such a sleeve 20 with two axially spaced apart, respectively annular, compression zones 31, 32 that extend over the entire circumference of the sleeve 20 and have been achieved by plastic deformation of said sleeve. The plastic deformation may be accomplished by two or more clamping jaws that are moved radially inward during the compression process accommodating the sleeve 20 between them, by a rolling tool comprising one roll, or several such rolls, that circulate around the circumference of the compression sleeve 20 one or more times. Furthermore, the sleeve can be constructed—in parts or in full—by electromagnetic forming with the use of a pulsed magnetic field, i.e., deformed radially inward. In doing so, as a matter of principle, no mechanical contact relative to the workpiece is necessary, so that surface contaminations of the sleeve can be precluded. The method can be used under clean room conditions.

Additionally or alternatively, it is possible in the case of all the aforementioned embodiments to secure the sleeve 20 with a suitable connecting means, for example an adhesive, to the tube end 19. This may be a two-component adhesive (polyurethane adhesive or epoxy adhesive), highly elastic cyanoacrylate, a UV-curable adhesive, an aerobically curable adhesive, an anaerobically curable adhesive or a solvent-containing adhesive. To promote adhesion, the tube end 19 may be preconditioned. This may be accomplished, for example, by roughening, plasma activation or by means of a primer. Preferably, however, an adhesive will be dispensed with.

The nozzle 24 (i.e., in particular the nozzle shaft 24a) is preferably also held by press-fitting. To accomplish this, the nozzle 24 may have a slightly greater outside diameter than the first lumen 16 in which said nozzle is held. Additionally or alternatively, the press-fit may also occur by constricting the lumen 16 by compression—at least in some zones, such compression being applied from the sleeve 20 radially inward toward the tube end 19.

After attaching the nozzle 24 and the sleeve 20 to the tube end 19, the end cap 21 is mounted. In order to facilitate positioning, said end cap may have one annular or several, e.g. three, finger-shaped extensions, or extensions in the shape of tabs, that extend over the part of the sleeve 20 that projects over the distal face surface 18. The extension may also be configured as an annular extension exhibiting one or more discontinuities. The initially attached end cap 21 can then be joined, by means of a suitable joining or welding process, for example laser welding, to the sleeve 20 in a fluid-tight manner.

Figure 11:
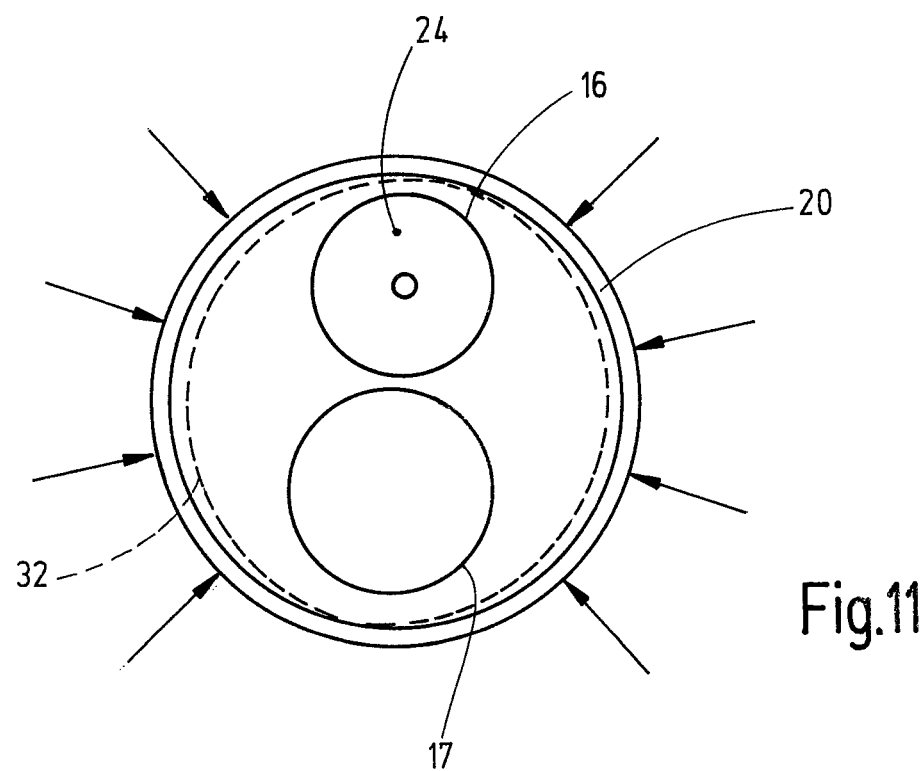
FIG. 11 a frontal view of the cryoprobe without end cap to illustrate the sleeve assembly process.

FIG. 11 illustrates the formation of the compression zone 32 in dashed lines. As is obvious, the depth of the compression zone 32 may vary around the circumference of the sleeve 20. For example, the depth of the compression zone 32 in the immediate vicinity of the channels 16, 17 may be reduced in order to maintain a deformation, in particular a constriction, of the channels, 16, 17, within limits. It is also possible to reduce the depth of the compression zone 32 only in the region of the second channel 17 in order to prevent the second channel 17 from collapsing while the compressive action on the first channel 16 promotes the secure fit of the nozzle 24 in the first channel 16.

Figure 9:
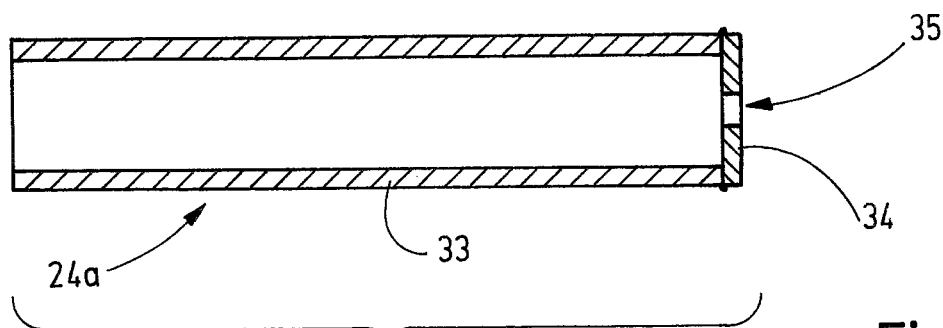
FIGS. 9 and 10 longitudinal sections of various embodiments of nozzles for the cryoprobe.
Figure 10:
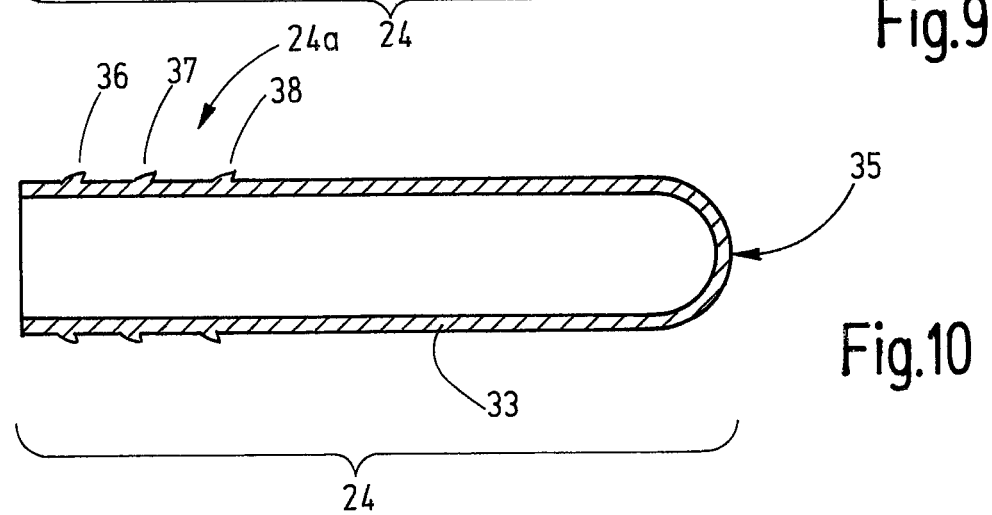

Furthermore, it is possible to additionally secure the nozzle 24 in axial direction in the channel 16. FIG. 9 shows a nozzle 24 that has a pipe section 33 with a smooth wall, said pipe section being closed on one end by a small nozzle plate 34 that has at least one nozzle orifice 36. The nozzle plate 34 can be welded to the pipe section 33, for example by laser-welding. However, it is also possible to constrict the distal end of the pipe section 33 during a forming process instead of using the small nozzle plate 34 in order to thus form a constricted nozzle orifice 35. The constriction relative to the pipe section 33 may be coaxial or also asymmetrical, e.g., eccentric, or extend along an axis oriented obliquely with respect to the axial direction of the pipe section 33.

In both cases, the structures for axially securing the nozzle in the lumen 16 may be configured, for example, as annular denticulated ribs 36, 37, 38, by one or more helix-type ribs, nubs, irregular structures such as rough areas or knurling.

The first channel 16 is disposed for the fluid flow, i.e., the supply of the nozzle 24 with liquid or gaseous cryofluid. The second channel 17 is disposed for the removal of the cryofluid from the expansion chamber 23. In order to minimize or prevent a constriction of the second channel 17 in particular in the region of the sleeve, it is possible to provide a support structure 39 in the tube end 19 or along the entire channel 17. FIG. 5 is a schematic illustration of such a structure. There, the support structure 39 consists of a lining of plastic material of the second channel 17, as can be inferred from FIG. 7. While the plastic tube 15 may generally consist of polyamides, polyolefins, Pebax, polyurethane, PEEK, PI, composite materials or other plastic materials, the support structure 39 may consist of a comparatively stiffer plastic material or of a metal braiding. If the support structure is restricted to the tube end 19, said structure may also consist of a metal pipe.

Figures 7, 8:
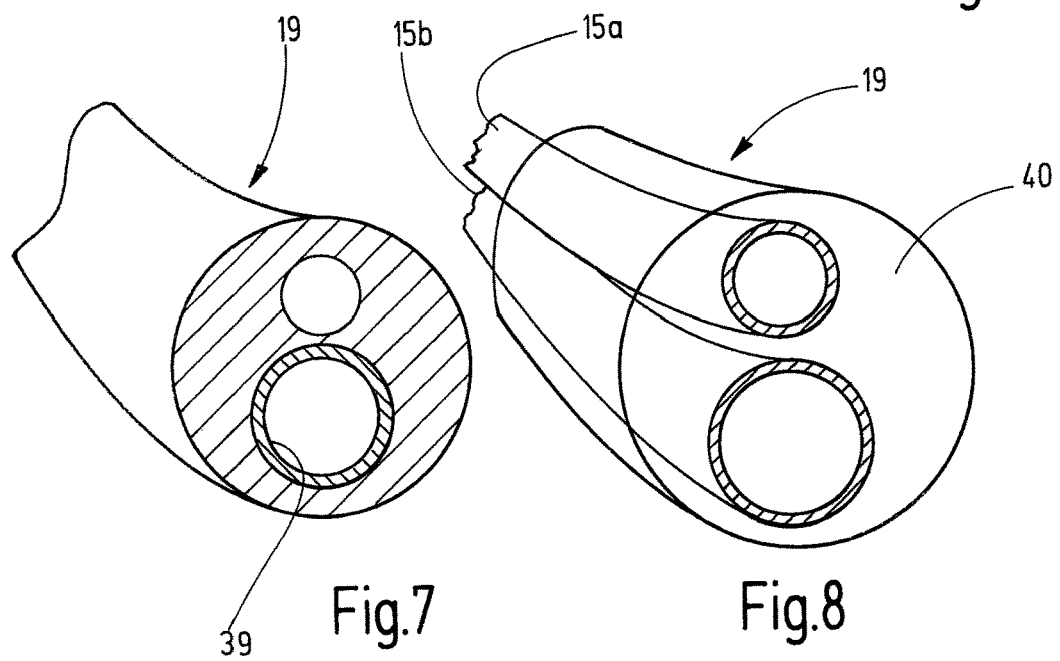

As shown in FIG. 8, the tube device 14 may also be made of several, for example two, plastic tubes 15, 15b that have the same or different diameters and are embedded in the head of a body, preferably a plastic body 40. This then forms the tube end 19, while—other than that—the description hereinabove applies accordingly.

Figure 4:
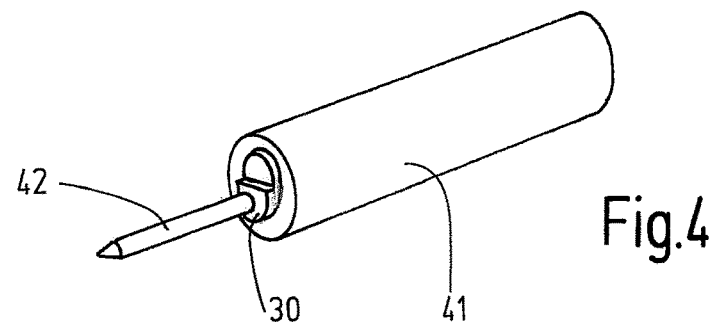
FIG. 4 an alternative embodiment of an assembly pin for performing the method.
Figure 6:
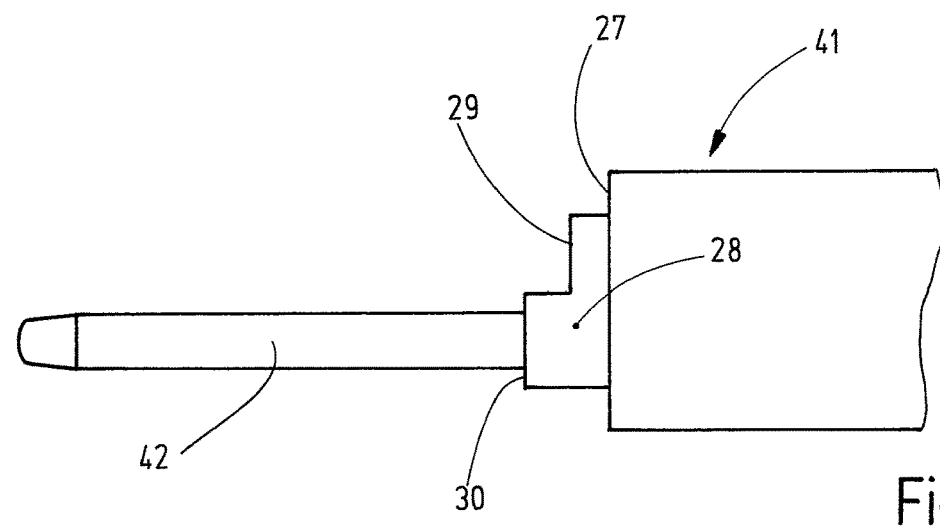
FIG. 6 a side view of the assembly pin according to FIG. 4.

The manufacture, in particular the joining of the tube end 19 to the nozzle 24 and the sleeve 20 may, in a more refined embodiment, alternatively also take place with the use of an assembly pin 41 according to FIGS. 4 and 6. In this case, a support pin 42 is arranged on the second abutment surface 30, said support pin having an outside diameter that substantially corresponds to the inside diameter of the second channel 17 or is slightly smaller than it. Referring to this assembly, the support pin 41 moves into the second channel 17 and remains in the channel 17, in particular also during the radially inward deformation of the sleeve 20 in the channel 17. In doing so, the support pin 42 prevents the channel 17 from collapsing or from being to much constricted as a result of the inward-directed deformation of the sleeve 40.

The manufacturing methods described so far may be additionally modified.

The support pin 42 can be disposed for the accommodation of a thin-walled small tube that comes into abutment with the face-side abutment on the second abutment surface 30 and is inserted into the second channel 17 during the joining process in order to, there, prevent the second channel 17 from collapsing during the radially inward-directed deformation of the sleeve 20. Furthermore, it is possible to configure the projection 28 without offset, in which case the abutment surface 29 is provided in a recess of the abutment surface 30. The recess, whose bottom is the abutment surface 29, is then disposed for the accommodation of the distal end of the nozzle 24 that is then inserted into the first lumen 16 during the joining process. The depth of the recess, in turn, determines the overlap of the nozzle 24 beyond the distal face surface 18 in the fully assembled state. This embodiment can be implemented on the assembly pin 25 according to FIG. 3, as well as on the assembly pin 41 according to FIGS. 4 and 6. The recess may be round in order to accommodate cylindrical, rotation-symmetrical nozzles. If the nozzles are not rotation-symmetrical because—maybe—the nozzle orifice is configured so as to be eccentric or extending in an oblique orientation, the nozzle may have a twist protection structure and, matching therewith, e.g., a lug or a recess, or be non-round in another suitable manner. Then, the recess has a correspondingly non-round form.

The inventive method of manufacturing a cryoprobe uses an assembly pin 25 for receiving a sleeve 20 that is to form a part of the head 13 of the cryoprobe and comprises three abutment surfaces 27, 29, 30 that are axially offset relative to each other, said abutment surfaces ensuring, following the attachment of the sleeve 20 and the nozzle 24 to the tube end 19, the correct axial positioning of the nozzle 24 and the sleeve 20, in particular, relative to the distal end surface 18 of the tube end 19. Consequently, the position of the nozzle 24 in the expansion chamber 23 that formed after the sleeve 20 was closed and thus the function of the cryoprobe are ensured.

| List of reference signs: | |
| --- | --- |
| 12 | Cryoprobe |
| 13 | Head of the cryoprobe 12 |
| 14 | Tube device |
| 15 | Double-lumen plastic tube |
| 16 | First channel of the tube device 14 |
| 17 | Second channel of the tube device 14 |
| 18 | Distal face side of the plastic tube 15 |
| 19 | Tube end of the plastic tube 15 |
| 20 | Sleeve |
| 21 | End cap |
| 22 | Laser weld seam |
| 23 | Expansion chamber |
| 24 | Nozzle |
| 24a | Nozzle shaft |
| 25 | Assembly pin |
| 26 | Sleeve receptacle |
| 27 | Compression surface |
| 28 | Projection/seat |
| 29 | First abutment surface of the projection 28 |
| 30 | Second abutment surface of the projection 28 |
| 31, 32 | Compression zones |
| 33 | Smooth-walled pipe section |
| 34 | Nozzle plate |
| 35 | Nozzle orifice |
| 36, 37, 38 | Denticulated ribs |
| 39 | Support structure |
| 40 | Plastic body |
| 41 | Assembly pin |
| 42 | Support pin |

What is claimed is:

1. Cryoprobe (12) apparatus comprising:

a tube device (14) that has a first channel (16) having arranged, in its distal end, a nozzle (24) with a nozzle shaft (24a) so that the nozzle (24) projects beyond an end of the first channel (16) and the nozzle shaft (24a) is inserted into a length of the first channel (16), and the tube device (14) also has a second channel (17) arranged at least parallel to and at a distance from the first channel (16), said second channel having a cross-section that is greater than a cross-section of one or both of the nozzle (24) and the first channel (16), a sleeve (20) that is arranged on a distal tube end (19) of the tube device (14) and that has an inside clearance which—at least in a completely assembled state—is smaller than an outside diameter of the tube device (14), and an end cap (21) that is arranged on a distal end of the sleeve (20) such that the end cap (21) closes said sleeve, wherein the sleeve (20) either is deformed radially inward in at least one compression zone (31, 32) where the distal tube end (19) is compressed or has an inside diameter smaller than the outside diameter of the tube device (14) such that the tube device (14) where the tube device (14) overlaps with the sleeve (20) is compressed, which includes the at least one compression zone (31, 32), and wherein the at least one compression zone (31, 32) at least partially overlaps the length of the first channel (16) in which the nozzle shaft (24a) is inserted such that compression of the distal tube end (19) compresses at least a portion of the first channel (16) against the nozzle shaft (24a).

2. Cryoprobe according to claim 1, wherein the sleeve (20) is held on the tube end (19) by press-fit.

3. Cryoprobe according to claim 1, wherein the sleeve (20) and the end cap (21) are connected to each other in a fluid-tight manner due to a tight connection.

4. Cryoprobe according to claim 1, wherein the sleeve (20) and the end cap (21) are made together, without seam and in one piece.

5. Cryoprobe according to claim 1, wherein the nozzle (24) is provided with an anchoring structure (36, 37, 38).

6. Cryoprobe according to claim 1, wherein the nozzle (24) is arranged so as to extend through the sleeve (20) or the at least one compression zone (31, 32).

7. Cryoprobe according to claim 1, wherein the second channel (17) is provided with a support structure (39).

8. Cryoprobe according to claim 1, wherein the sleeve (20) is deformed radially inward in the at least one compression zone (31, 32) where the tube end (19) is compressed.

* * * * *